(12) United States Patent
Ho et al.

(10) Patent No.: US 8,066,510 B2
(45) Date of Patent: Nov. 29, 2011

(54) DENTAL AGENT APPLICATOR

(75) Inventors: Phillip Phung-I Ho, Santa Barbara, CA (US); Chung-Chieh Lee, Taipei Hsien (TW)

(73) Assignee: Phillip Phung-I Ho, Santa Barbara, CA (US)

( * ) Notice: Subject to any disclaimer, the term of this patent is extended or adjusted under 35 U.S.C. 154(b) by 303 days.

(21) Appl. No.: 12/423,676

(22) Filed: Apr. 14, 2009

(65) Prior Publication Data

US 2010/0261138 A1    Oct. 14, 2010

(51) Int. Cl.
*A61C 5/04* (2006.01)

(52) U.S. Cl. .......................................... 433/90

(58) Field of Classification Search .............. 433/80–90; 604/240, 241; 12/78, 560
See application file for complete search history.

(56) References Cited

U.S. PATENT DOCUMENTS

| | | | |
|---|---|---|---|
| 1,683,349 A * | 9/1928 | Hein | 604/241 |
| 4,578,055 A | 3/1986 | Fischer | |
| 4,997,371 A | 3/1991 | Fischer | |
| 5,269,684 A | 12/1993 | Fischer | |
| 5,286,257 A * | 2/1994 | Fischer | 604/82 |
| 7,128,246 B2 * | 10/2006 | Raia et al. | 222/327 |

* cited by examiner

*Primary Examiner* — Cris L Rodriguez
*Assistant Examiner* — Mirayda A Aponte
(74) *Attorney, Agent, or Firm* — Hershkovitz & Associates, LLC; Abraham Hershkovitz

(57) ABSTRACT

A dental agent applicator has a barrel, a sealing plug, a delivery head and a plunger. The barrel has a proximal end, a distal end and a chamber defined through the barrel. The sealing plug is mounted in the chamber and hermetically obstructs the chamber. The delivery head is movably mounted on the distal end of the barrel and has a hub and a nozzle tip. The hub is mounted movably in the distal end and selectively moves the sealing plug to make the chamber communicate with the delivery head. The nozzle tip is mounted on the hub. The plunger is mounted slidably in the proximal end of the barrel. The delivery head is mounted permanently on the barrel. Using the dental agent applicator without having to replace any sealing cap with the delivery head is simple and convenient.

3 Claims, 5 Drawing Sheets

DENTAL AGENT APPLICATOR

BACKGROUND OF THE INVENTION

1. Field of the Invention

The present invention relates to an applicator, and more particularly to a dental agent applicator that has a barrel and a delivery head mounted permanently on the barrel and using the dental agent applicator requires no need to detach or attach any other components.

2. Description of Related Art

Dental agent such as bonding agent is applied to a tooth surface to firmly attach a dental restoration to the tooth surface.

Dental agent applicators are disposable and are used to store and apply dental agent to a tooth surface. U.S. Pat. Nos. 4,578,055 and 4,997,371 discloses conventional dental applicators having a barrel, a plunger and a delivery tip. The barrel receives dental agent. The delivery tip is mounted on a front end of the barrel and has a brush mounted therein. Before use, a sealing cap covers the front end of the dental agent applicator. Right before use, the sealing cap is replaced with the delivery tip. After use, the delivery tip is replaced by the sealing cap and stored away.

U.S. Pat. No. 5,269,684 discloses another conventional dental agent applicator being similar to the aforementioned applicators and modifying the delivery tip. The modified delivery tip has a passageway and a helical ridge formed in the passageway to hold the brush in place. A sealing cap covers the front end off the barrel before using the applicator.

However, the delivery tips of aforementioned applicator does not have any sealing function so that the airtight sealing cap is necessarily mounted on the applicator to prevent oxidation or evaporation of the liquid dental agent. Therefore, replacing the sealing cap with the delivery tip wastes time. A package including the applicator, delivery tip, and sealing cap is cumbersome such that storing, transporting, or using such packages is inconvenient and costly.

To overcome the shortcomings, the present invention provides a dental agent applicator to mitigate or obviate the aforementioned problems.

SUMMARY OF THE INVENTION

The main objective of the invention is to provide a dental agent applicator that has a barrel and a delivery head mounted permanently on the barrel and using the dental agent applicator would not require detaching or attaching any components.

A dental agent applicator in accordance with present invention comprises a barrel, an internal sealing plug, a delivery head, and a plunger. The barrel has a proximal end, a distal end and a chamber defined through the barrel. The sealing plug is mounted in the chamber and hermetically obstructs the chamber. The delivery head is movably mounted on the distal end of the barrel and has a hub and a nozzle tip. The hub is movably mounted on the distal end and selectively moves the sealing plug to make the chamber communicate with the delivery head. The nozzle tip is mounted on the hub. The plunger is mounted slidably in the proximal end of the barrel. The delivery head is mounted permanently on the barrel. Using the dental agent applicator without replacing any sealing cap with the delivery head is simple and convenient.

Other objectives, advantages and novel features of the invention will become more apparent from the following detailed description when taken in conjunction with the accompanying drawings.

DETAILED DESCRIPTION OF THE PREFERRED EMBODIMENT

Figure 1:
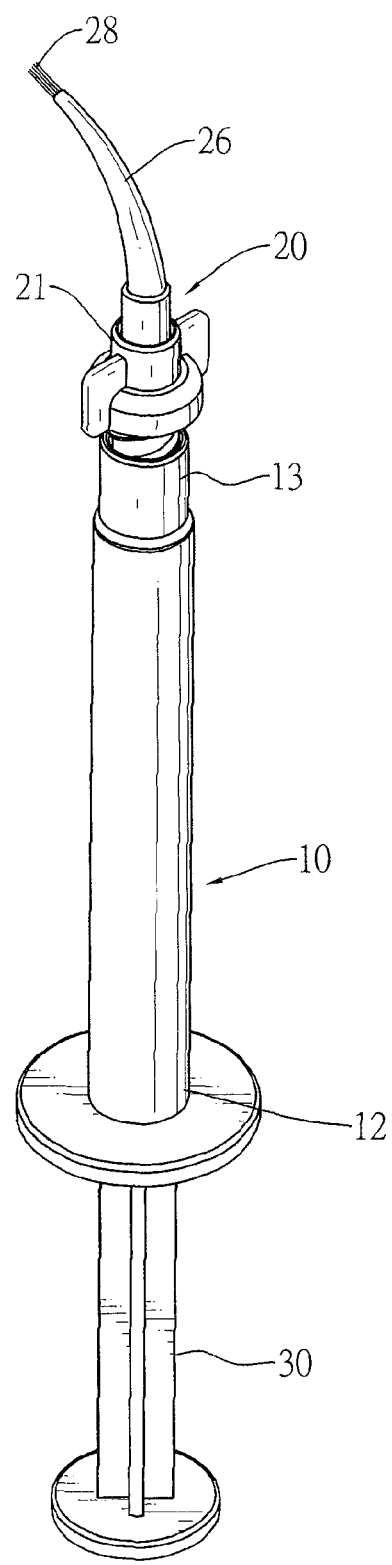
FIG. 1 is a perspective view of a dental agent applicator in accordance with the present invention before use.
Figure 3:
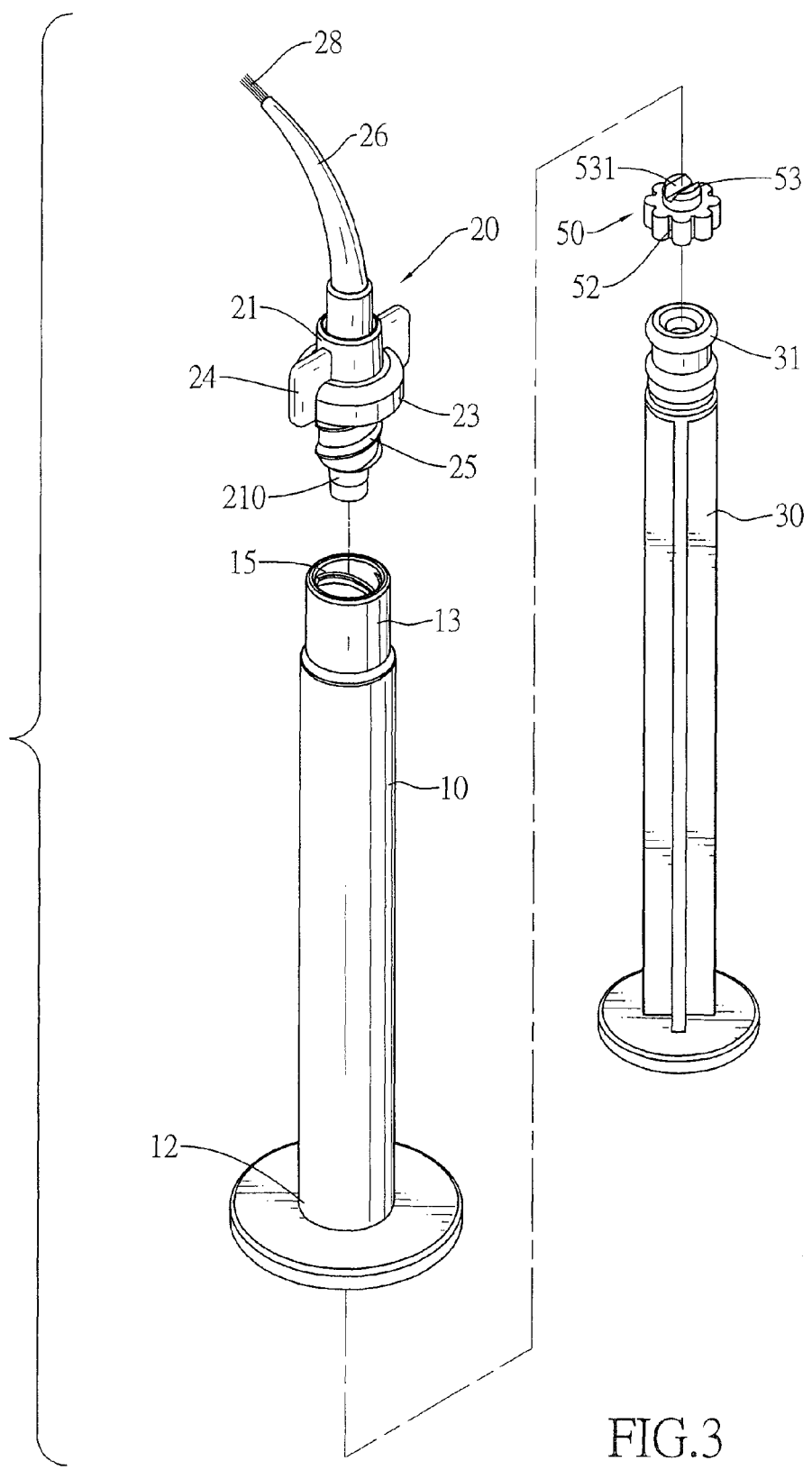
FIG. 3 is an exploded perspective view of the dental agent applicator in FIG. 1.

With reference to FIGS. 1 and 3, a dental agent applicator in accordance with the present invention may be filled with a dental agent (60) such as bonding agent for firmly attaching a dental restoration to a tooth surface.

The dental agent applicator comprises a barrel (10), a sealing plug (50), a delivery head (20) and a plunger (30).

Figure 4:
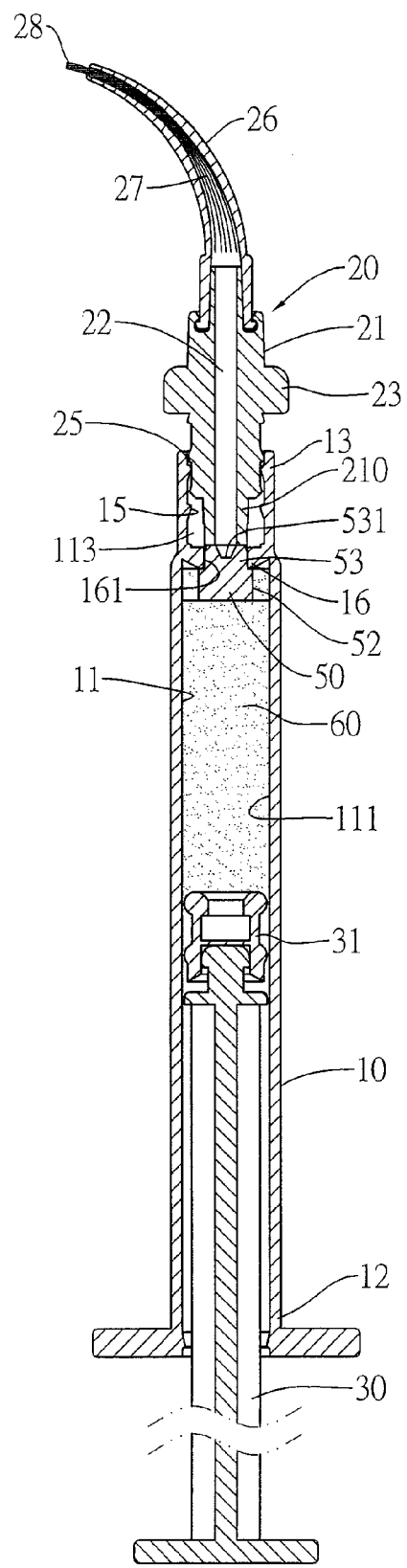
FIG. 4 is a cross sectional side view of the dental agent applicator in FIG. 1.

With further reference to FIG. 4, the barrel (10) is hollow and has a proximal end (12), a distal end (13), a chamber (11) and an inner annular flange (16) and may further have an inner thread (15).

The chamber (11) is defined axially and longitudinally through the barrel (10), receives the dental agent (60) and has an inner surface.

The inner annular flange (16) is formed on and protrudes radially inward from the inner surface of the chamber (11) close to the distal end (13) and divides the chamber (16) into an inside space (111) and an outside space (113). The inside space (111) is located adjacent to the proximal end (12). The outside space (113) is located adjacent to the distal end (13). The inner annular flange (16) has a central hole (161) defined through the inner annular flange (16) and communicating with the chamber (11).

The inner thread (15) is formed on the inner surface of the chamber (11) between the distal end (13) and the inner annular flange (16) and may be adjacent to the distal end (13).

The sealing plug (50) is circular, is mounted in and selectively hermetically obstructs the chamber (11) of the barrel (10), is engaged hermetically and detachably with the central hole (161) of the inner annular flange (16) to isolate the inside space (111) from the outside space (113) of the chamber. The sealing plug (50) may have an annular outer edge, multiple notches (52) and a cylinder stopper (53). The notches (52) are defined radially in the annular outer edge so that the dental agent (60) in the inside space (111) of the chamber (11) flows fluently through the notches (52) when the sealing plug (50) disengages from the central hole (161) of the inner annular flange (16). The cylinder stopper (53) is formed on and protrudes axially from the sealing plug (50), is mounted detachably in and seals the central hole (161) of the inner annular flange (16) and may have a distal end and a cutout (531) defined in the distal end. The cutout (531) makes the cylinder stopper (53) resilient and compressible so that the cylinder stopper (53) may be withdrawn easily out from the central hole (161).

When the sealing plug (50) is engaged hermetically with the central hole (161), the inside space (111) is isolated from the outside space (113) to keep the dental agent (60) in the inside space (111) from flowing into the outside space (113).

Figure 2:
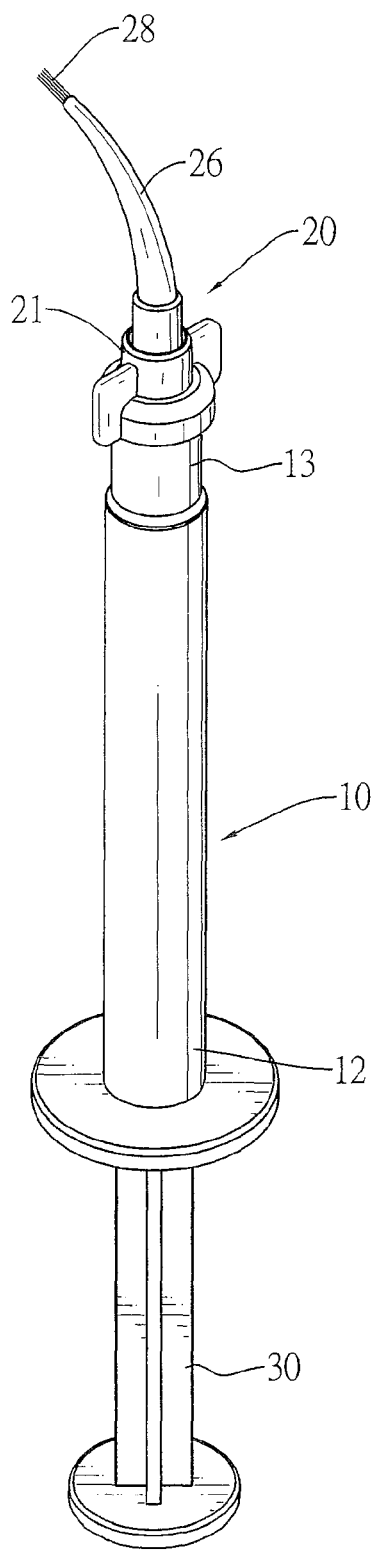
FIG. 2 is an operational perspective view of the dental agent applicator in FIG. 1 with the delivery head screwed tightly on the distal end of the barrel to open the sealing plug in the barrel to allow free flow of the dental agent.
Figure 5:
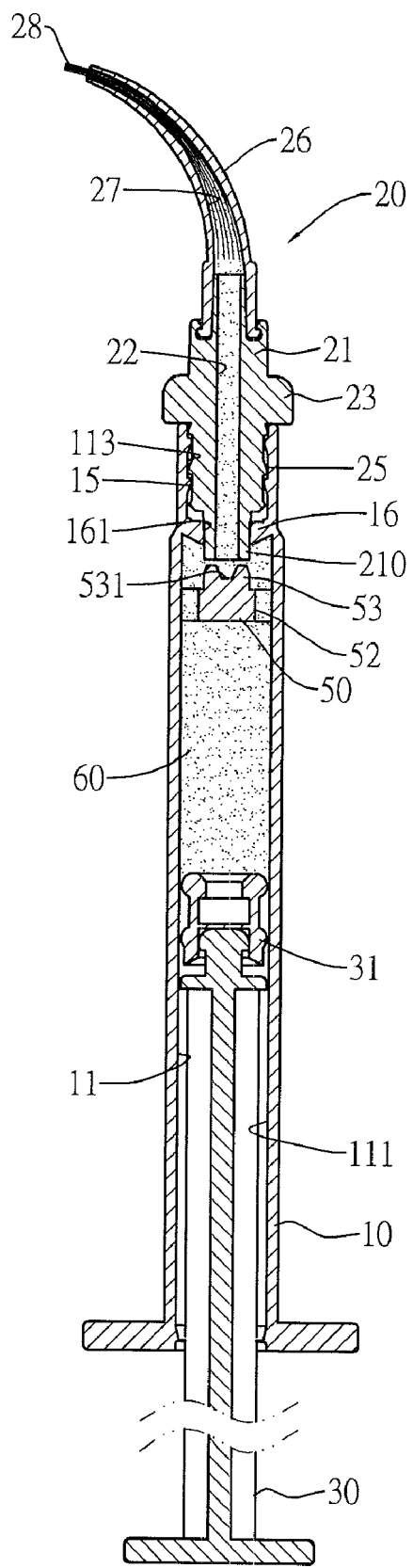
FIG. 5 is an operational cross sectional side view of the dent agent applicator in FIG. 2.

With further reference to FIGS. 2 and 5, when the sealing plug (50) disengages from the central hole (161), the inside space (111) communicates with the central hole (161) and the outside space (113) so that the dental agent (60) flows through the central hole (161).

The delivery head (20) is tapered, is mounted movably on the distal end (13) of the barrel (10), may be screwed into the distal end (13) of the barrel (10) and has a hub (21) and a nozzle tip (26) and may further have a brush (28).

The hub (21) is hollow, is mounted movably in the distal end (13) into the chamber (11) of the barrel (10) and selectively moves the sealing plug (50) to un-obstruct and make the chamber (11) communicate with the hub (21). The hub (21) selectively presses against and disengages the sealing plug (50) from the central hole (161) of the inner annular flange (16). The hub (21) has an outside end, an inside end and a channel (22). The hub (21) may further have a connecting tube (210), an outer thread (25), a shoulder (23) and a thumb knob (24). The channel (22) is defined through the hub (21) and selectively communicates with the inside space (111) of the chamber (11) depending whether the sealing plug (50) disengages from the central hole (161) of the inner annular flange (16) or not. The connecting tube (11) is formed on and protrudes longitudinally from the inside end of the hub (21), communicates with the channel (22) and selectively pushes the cylinder stopper (53) of the sealing plug (50) out of the central hole (161) of the inner annular flange (16) and is simultaneously mounted in the central hole (161) to make the channel (22) communicate with the inside space (111) of the chamber (11). The outer thread (25) is formed on the hub (21) adjacent to the connecting tube (210) and is engaged with the inner thread (15) of the barrel (10) to selectively and longitudinally move the hub (21) in the distal end (13) of the barrel (10). The shoulder (23) may be annular, is formed on and protrudes radially from the hub (21) and selectively abuts against the distal end (13) of the barrel (10). The thumb knob (24) may be two opposite wings, is formed on and protrudes radially from the hub (21) to facilitate the manual rotation of the delivery head (20).

The nozzle tip (26) is hollow, may be curved, is mounted on the outside end of the hub (21) and has an outlet end and a passageway (27). The passageway (27) is defined through the nozzle tip (26) and the channel (22) of the hub (21).

The brush (28) is mounted in the passageway (27) and extends out of the outlet end of the nozzle tip (26).

The plunger (30) is mounted slidably in the chamber (11) from the proximal end (12) of the barrel (10) and has an inside end and an enlarged head (31). The enlarged head (31) is resilient, may be rubber, is mounted on the inside end and hermetically contacts the inner surface of the chamber (11).

With reference to FIGS. 1 and 4, the sealing plug (50) seals the central hole (161) of the barrel (16) before the dental agent applicator is used so that the dental agent (60) is kept in the inside space (111) and would not flow out of the delivery head (20).

With reference to FIGS. 2 and 5, when the dental agent applicator is used, the delivery head (20) is moved or screwed tightly to extend deeper into the distal end (13) of the barrel (10) so that the connecting tube (210) pushes and detaches the sealing plug (50) out from the central hole (161) of the inner annular flange (16). The dental agent (60) extruded by the plunger (30) flows through the notches of the sealing plug (50) then is extruded out of the nozzle tip (26) of the delivery head (20).

With the sealing plug (50) inside the barrel (10), the dental agent applicator would not need a sealing cap to hermetically cover the distal end (13) of the barrel (10). The delivery head (10) is always mounted on the distal end (16) of the barrel (10) without being troublesomely removed and replaced beforehand with any sealing cap. When the dental agent applicator is used, simply screwing and tightening the delivery head (20) would easily disengage the sealing plug (50) and make the barrel (10) communicate with the delivery head (20). Therefore, using the dental agent applicator without replacing any sealing cap with the delivery head (20) is simple and convenient.

Even though numerous characteristics and advantages of the present invention have been set forth in the foregoing description, together with details of the structure and function of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A dental agent applicator comprising:
    a barrel being hollow and having
        a proximal end;
        a distal end; and
        a chamber defined axially and longitudinally through the barrel and having an inner surface;
    a sealing plug mounted in and selectively obstructing the chamber of the barrel;
    a delivery head mounted movably on the distal end of the barrel and having
        a hub being hollow, mounted movably in the distal end into the chamber of the barrel and selectively moving the sealing plug to un-obstruct and make the chamber communicate with the hub and having an outside end and an inside end; and
        a nozzle tip being hollow and mounted on the outside end of the hub; and
    a plunger mounted slidably in the chamber from the proximal end of the barrel;
    wherein the barrel further has an inner annular flange formed on and protruding radially inward from the inner surface of the chamber close to the distal end and dividing the chamber into an inside space and an outside space located adjacent to the distal end, and the inner annular flange has a central hole defined through the inner annular flange and communicating with the chamber;
    wherein the sealing plug is engaged hermetically and detachably with the central hole of the inner annular flange;
    wherein the hub of the delivery head selectively presses against and disengages the sealing plug from the central hole of the inner annular flange and further has a channel defined through the hub and selectively communicating with the inside space of the chamber;
    wherein the nozzle tip of the delivery head has an outlet end and a passageway defined through the nozzle tip and communicating with the channel of the hub;
    wherein the barrel further has an inner thread formed on the inner surface of the chamber between the distal end and the inner annular flange;
    wherein the delivery head is screwed into the distal end of the barrel and the hub further has an outer thread formed on the hub and engaged with the inner thread of the barrel to selectively and longitudinally move the hub in the barrel;
    wherein the sealing plug has an annular outer edge, multiple notches defined radially in the annular outer edge, and a cylinder stopper formed on and protruding axially from the sealing plug, mounted detachably in and sealing the central hole of the inner annular flange; and wherein the hub further has a connecting tube formed on and protruding longitudinally from the inside end of the hub, located adjacent to the outer thread, communicating with the channel and selectively pushing the cylinder stopper of the sealing plug out of the central hole of the inner annular flange and simultaneously mounted in the central hole.

2. The dental agent applicator as claimed in claim 1, wherein the hub further has
   a shoulder formed on and protruding radially from the hub and selectively abutting against the barrel; and
   a thumb knob formed on and protruding from the hub.

3. The dental agent applicator as claimed in claim 2, wherein the delivery head further has a brush mounted in the passageway and extending out of the outlet end of the nozzle tip.

* * * * *